United States Patent [19]

Holick et al.

[11] Patent Number: 5,167,953

[45] Date of Patent: Dec. 1, 1992

[54] COMPOSITIONS COMPRISING TACHYSTERAL AND THE USE THEREOF TO PROVIDE VITAMIN D

[75] Inventors: Michael F. Holick, Sudbury; Zhiren Lu; Xiao Q. Tian, both of Boston, all of Mass.

[73] Assignee: Trustees of Boston University, Boston, Mass.

[21] Appl. No.: 541,812

[22] Filed: Jun. 21, 1990

[51] Int. Cl.⁵ .................. A61K 7/42; A61K 31/59; A61K 7/44; A61K 31/70
[52] U.S. Cl. ........................... 424/59; 514/167; 514/25; 514/54; 424/60
[58] Field of Search ............ 514/167, 25, 54; 552/653; 424/59, 60

[56] References Cited

U.S. PATENT DOCUMENTS

| | | | |
|---|---|---|---|
| 4,230,701 | 10/1980 | Holick et al. | 514/167 |
| 4,310,511 | 1/1982 | Holick | 514/171 |
| 4,335,120 | 6/1982 | Holick et al. | 514/167 |
| 4,619,829 | 10/1986 | Motschan | 424/128 |
| 4,686,023 | 8/1987 | Stevens | 204/157.67 |
| 4,937,292 | 6/1990 | Slemon | 525/326.8 |

OTHER PUBLICATIONS

Dauben, W. G. et al., *J. Am. Chem. Soc.* 104:355–356 (1982).
Dauben, W. G. et al., *J. Am. Chem. Soc.* 104:5780–5781 (1982).
Holick, M. F. et al., *Science* 210:203–205 (1980).
Holick, M. F. et al., *Science* 211:590–593 (1981).
McLaughlin, J. A. et al., *Science* 216:1001–1003 (1982).
Malatesta, V. et al., *J. Am. Chem. Soc.* 103:6781–6783 (1981).

*Primary Examiner*—Frederick E. Waddell
*Assistant Examiner*—Kimberly Jordan
*Attorney, Agent, or Firm*—Sterne, Kessler, Goldstein & Fox

[57] ABSTRACT

Methods for providing vitamin D to an individual with compositions comprising tachysterol and derivatives thereof are disclosed. Also disclosed are pharmaceutical compositions comprising tachysterol which may be administered topically or by intravenous means.

17 Claims, 4 Drawing Sheets

COMPOSITIONS COMPRISING TACHYSTERAL AND THE USE THEREOF TO PROVIDE VITAMIN D

FIELD OF THE INVENTION

The invention is in the field of cosmetics and medicinal chemistry. In particular, the present invention relates to topical compositions which provide vitamin D and derivatives thereof throughout the year. In another aspect, the present invention relates to a method of producing previtamin D. The topical compositions of the invention allow a user in the high northern and southern latitudes to produce previtamin D on their skin even when exposed to low energy sunlight in the winter as well as in the morning and evening throughout the year. The method employs tachysterol and lumisterol and derivatives thereof which photoisomerize to previtamin D and derivatives thereof when exposed to low levels of ultraviolet radiation.

BACKGROUND OF THE INVENTION

Vitamin $D_3$ is a derivative of provitamin $D_3$ (7-dehydrocholesterol), the immediate biological precursor of cholesterol. With adequate exposure to sunlight, dietary supplements are not normally required. Holick et al. in Braunwald et al., Harrison's Principles of Internal Medicine, 11th ed. McGraw-Hill (1987), pp. 1857–69. However, not all individuals are exposed to the adequate levels of sunlight, especially in the winter.

When skin is exposed to sunlight or artificial sources of ultraviolet (UV) radiation, the UV radiation penetrates the epidermis and causes a variety of biochemical reactions. Included in these reactions include the transformation of provitamin $D_3$ to previtamin $D_3$. The solar electromagnetic energy having wavelengths between 290 and 315 nm is absorbed by provitamin $D_3$ resulting in its fragmentation to previtamin $D_3$. Although previtamin $D_3$ is biologically inert, it is thermally labile and spontaneously undergoes a temperature-dependent rearrangement to form the thermally stable vitamin $D_3$. After biosynthesis, vitamin $D_3$ is translocated from the epidermis into the circulation via a vitamin-D binding protein. Holick et al. Science 211:590–593 (1981); Holick et al. in Braunwald et al., Harrison's Principles of Internal Medicine, 11th ed., McGraw-Hill (1987), pp. 57–69.

Factors that are frequently considered as affecting the cutaneous synthesis of vitamin $D_3$ include age, altitude, geographical location, time of day, seasonal changes and area of exposure to sunlight. Common to most of these factors is the availability of the requisite amount of ultraviolet radiation with energies between 290 and 315 nm which is necessary to convert provitamin $D_3$ to previtamin $D_3$. MacLaughlin et al., Science 216:1001–1003 (1982).

The availability of a vitamin D precursor (provitamin $D_3$) in the skin and its photo-induced transformation to previtamin $D_3$ and then to vitamin $D_3$ is an efficient physiological source of and mechanism for the replenishment of vitamin $D_3$. However, during the winter in northern latitudes, sunlight does not contain enough high energy ultraviolet radiation to convert provitamin $D_3$ (7-dehydrocholesterol) in human skin to previtamin $D_3$. As a result, individuals in these latitudes cannot make vitamin $D_3$ in their skin, even when they are exposed to sunlight. Webb, Kline and Holick, J. Clin. Endocrin. Met. 67:373–378 (1988). The lack of adequate exposure to ultraviolet radiation gives rise to the possibility of serious vitamin D deficiency, a breakdown in blood calcium regulation with concomitant hypocalcemia and bone calcium wasting.

The availability of the vitamin D precursor in the skin and its photo-induced transformation to previtamin $D_3$, and then to vitamin $D_3$, is an efficient physiological source of, and mechanism for the replenishment of vitamin $D_3$. Previously, it was thought that the only method of producing previtamin $D_3$ in the skin was to transform provitamin $D_3$. This transformation requires sunlight or artificial UV light in the region of 290–315 nm. Therefore, in areas where the available light energy is below this range (wavelengths greater than 316 nm), the transformation does not occur to any significant extent. Kobayashi et al., J. Nutr. Sci. Vitaminol. 19:123 (1973).

It has been disclosed (Holick, M., Transactions of the Association of American Physicians, 42:54–63 (1979); Molecular Endocrinology; MacIntyre and Szelke, eds.; Elsevier/North Holland Biomedical Press (1979), pp.301–308) that the topical application of hydroxylated metabolites of provitamin D compounds to the skin combined with U.V. phototherapy is a method for the sustained administration of vitamin D metabolites to patients who suffer vitamin D metabolic disorders. When the hydroxylated provitamins are applied and irradiated with ultraviolet radiation, they convert to hydroxylated previtamins which then thermally isomerize to the hydroxylated vitamin D. This work is also disclosed in Holick et al., New England Journal of Medicine 301:349–354 (1980) and U.S. Pat. No. 4,310,511 (Jan. 12, 1982).

Hungarian Patent No. 102,939 discloses cosmetic creams containing vitamin D precursors (such as ergosterol) which, when irradiated with ultraviolet rays, are transformed into vitamin D.

MacLaughlin et al., Science 216:100–1003 (1982), disclose the synthesis of previtamin $D_3$ from provitamin $D_3$ in human skin and in an organic solvent after exposure to narrow-band radiation or simulated solar radiation. When human skin or an organic solvent containing provitamin $D_3$ were exposed to 295 nm radiation, up to 65% of the provitamin $D_3$ was converted to previtamin $D_3$. The authors further disclose that the optimum wavelength for the production of previtamin $D_3$ is between 295 nm and 300 nm.

Dauben et al., J. Am. Chem. Soc. 104:5780–5781 (1982); J Am. Chem. Soc. 104:355–356 (1982), disclose the effect of wavelength on the photochemistry of provitamin $D_3$ and the effect of wavelength on the production of previtamin $D_3$. The authors found that when provitamin $D_3$ is exposed to light in the range of 254 nm, it is converted to a variety of photoproducts, the major portion being about 75% tachysterol. This mixture was then exposed to either 300 nm of light, broad-band 350 nm light or 355 nm light to give a build up of previtamin $D_3$. Dauben et al. conclude that if provitamin $D_3$ is first irradiated at 0° C. with 254 nm light to give a quasi photostationary state of provitamin $D_3$, previtamin $D_3$, tachysterol and lumisterol, and the mixture is thereafter irradiated (0° C.) with 350 nm light, a maximum of 83% previtamin $D_3$ is produced.

Malatesta et al., J. Amer. Chem. Soc. 103:6781–6783 (1981), disclose the effects of different UV wavelengths on the relative quantities of photoproducts produced from provitamin $D_3$.

Holick et al. disclose that the photochemical conversion of previtamin $D_3$ to lumisterol and tachysterol is the major factor that prevents vitamin $D_3$ intoxication after a single prolonged exposure to the sun. Holick et al., Science 211:590–592 (1981). The corollary to this finding is that lumisterol and tachysterol are two biologically inert products thought to be sloughed off the skin during the natural turnover of the epidermal cells.

Provitamin $D_2$ (ergosterol) is the precursor of vitamin $D_2$. Vitamin $D_2$ is one of the major forms of vitamin D that is used to fortify foods such as milk and multivitamins.

SUMMARY OF THE INVENTION

The present invention is related to the discovery that topical formulations comprising lumisterol and tachysterol and derivatives thereof are effective means of providing previtamin D to individuals. The present invention utilizes the low energy UV photo-conversion of lumisterol and tachysterol and derivatives thereof to previtamin D and derivatives thereof as a method of producing vitamin D in the skin. It is this novel finding that solves the problem of producing vitamin D via the skin in areas of low energy sunlight.

In particular, the invention is directed to a pharmaceutical composition containing an effective amount of lumisterol and or tachysterol and/or derivatives thereof, and a pharmaceutically effective carrier.

The invention is also directed to a method for providing vitamin D to an individual by administering to the individual a pharmaceutical composition of the invention.

DESCRIPTION OF THE PREFERRED EMBODIMENTS

Figure 1:
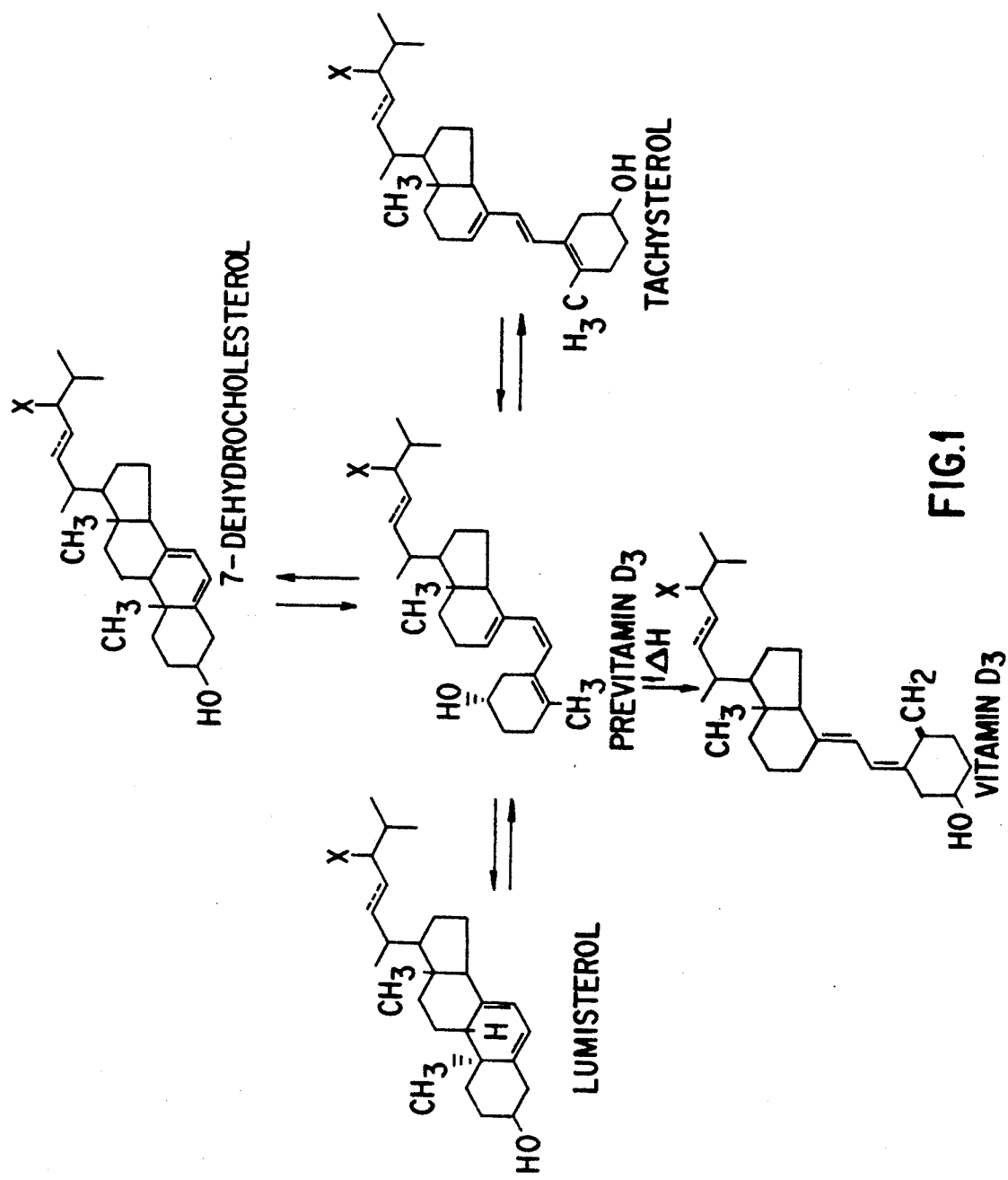
FIG. 1 illustrates the photochemical conversion of provitamin D to vitamin D and the concomitant production of lumisterol and tachysterol. When the bond between C-22 and C-23 is a single covalent bond and X is hydrogen, the compounds belong to the $D_3$ family, e.g. vitamin $D_3$. Where the bond between C-22 and C-23 is a double covalent bond and X is methyl, the compounds belong to the $D_2$ family, e.g. vitamin $D_2$.

The active compounds utilized in the present invention are tachysterol, lumisterol and derivatives thereof, either alone or in combination. The tachysterol and lumisterol derivatives have the following Formulae (I) and (II), respectively:

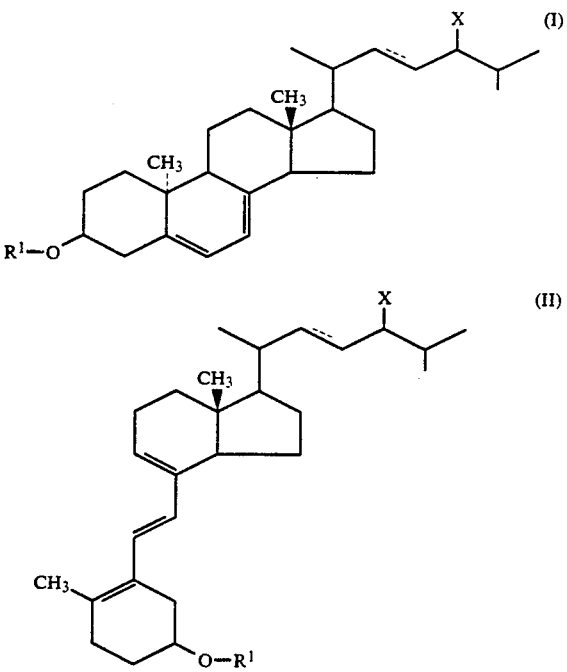

wherein the bond between C-22 and C-23 is a single or double bond;

X is hydrogen, methyl or ethyl; and $R^1$ is hydrogen or a straight or branched chain glycosidic residue containing 1-20 glycosidic units per residue, or $R^1$ is an orthoester glycoside moiety of the Formula (III):

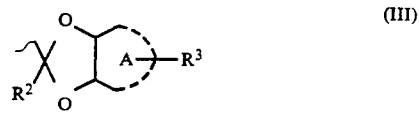

where A represents a glucofuranosyl or a glucopyranosyl ring;

$R^2$ is hydrogen, lower ($C_1$–$C_4$) alkyl, $C_7$–$C_{10}$ aralkyl, or $C_6$–$C_{10}$ aryl; and $R_3$ is hydrogen or a straight or branch chain glycosidic residue containing 1-20 glycosidic units per residue.

These compounds are photoisomers of previtamin D, the precursor of biologically active vitamin D. Tachysterol and lumisterol may be prepared by photoisomerization and isolation as disclosed by Holick et al., Biochem. 18:1003–1008 (1979), which is fully incorporated by reference herein. Analogous methods for making the corresponding glycosidic and orthoester glycoside derivatives are taught, for example, by Holick et al., U.S. Pat. Nos. 4,410,515 and 4,521,410, the disclosures of which are fully incorporated by reference herein.

Foremost among the individuals which may be treated with the compositions of the invention are humans, although the invention is not intended to be so limited. Any animal which may benefit from treatment with the compositions of the invention are within the spirit and scope of the present invention.

By using tachysterol, lumisterol and derivatives thereof in topical compositions according to this invention, it is possible for the first time to provide a method which allows individuals living in regions of low energy sunlight to produce vitamin D compounds via their skin, thus preventing harmful vitamin $D_3$ depletion. The compositions of the present invention may be used, therefore, in methods of treating or preventing osteomalacia due to vitamin D deficiency, and calcium disorders resulting from a lack of vitamin D (a lack of vitamin D leads to deficient intestinal absorption of calcium which results in hypocalcemia), glucocorticoid-induced decrease in calcium absorption, osteoporosis, senile decrease in calcium absorption, hypoparathyroidism, milk fever disease, turkey weak leg disease, etc.

The compounds of the present invention can be administered in any appropriate pharmacological carrier for topical or intravenous administration. The dosage administered will be dependent on the age, health and weight of the recipient, and the nature of the effect desired.

The topical compositions of the invention may be applied so that at least 0.1 microgram, preferably at least about 10 micrograms to about 100 mg of the vitamin D precursor/gm carrier is administered to the skin. A preferred range is between about 1 microgram to about 1 milligram of tachysterol or lumisterol/gm carrier.

The compositions of the invention formulated for intravenous administration may comprise at least about 0.1 microgram, preferably at least about 1.0 microgram to about 100 mg of the vitamin D precursor per ml of physiologically acceptable solution. A most preferred range is about 1.0 micrograms to about 100 micrograms of tachysterol or lumisterol per ml of solution.

The compounds can be employed in a pharmacologically inert topical carrier such as one comprising a gel, an ointment or a cream, including such carriers as water, glycerol, alcohol, propylene glycol, fatty alcohols, triglycerides, fatty acid esters or mineral oils. Other possible carriers are liquid petrolatum, isopropylpalmitate, polyethylene glycol ethanol 95%, polyoxyethylene monolaurate 5% in water, sodium lauryl sulfate 5% in water, and the like. Minerals such as anti-oxidants, humectants, viscosity stabilizers and the like may be added, if necessary.

Alternatively, the compounds may be employed as part of a sun screen lotion which selectively screens the harmful high energy UV radiation (below 315 nm) but which allows medium and low energy UV radiation (above 315 nm) to pass which is of sufficient energy to photoisomerize lumisterol and tachysterol to previtamin D. Alternatively, lumisterol, tachysterol and derivatives thereof may be added to broad range sun screens that absorb radiation with energies of up to 360 nm. Such sun screen lotions may comprise any of those well known to those of ordinary skill in the art, for example, ethyl p-aminobenzoate (benzocaine) p-aminobenzoic acid (PABA), octyl methoxycinnamate (PARASOL ® MCX), butyl methoxydibenzoylmethane (PARASOL ® 1789), phenyl salicylate (salcol), 2-ethoxyethyl p-methoxycinnamate, glyceryl p-aminobenzoate, 2,4-dibenzoyl resorcinol, octyl dimethyl PABA, oxybenzone, benzophenones, methyl anthranilate, cinoxate, amyldimethyl PABA, homomenthyl salicylate, digalloyl trioleate, ethyl-p-glycosylimido benzoate, and red veterinary petrolatum. For other examples, see Algra et al., *Int. J. Derm.* 17:628-634 (1978), Sayre, R. M. et al., *Photochem.Photobiol.* 29:559-566 (1979).

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, inert gases and the like. See, generally, *Remington's Pharmaceutical Science,* 16th Ed., Mack Eds., 1980.

The compositions comprising tachysterol, lumisterol and derivatives thereof which are formulated for parenteral administration may be utilized to provide an individual with these vitamin D precursors so as to allow the production of vitamin $D_3$ in the skin in the presence of medium and low energy UV radiation.

The invention further relates to solutions comprising tachysterol, lumisterol and derivatives thereof which may be exposed to UV radiation to allow the preparation of a solution comprising a vitamin D compound just before administration to the individual. This method avoids the decomposition of vitamin D compound just before administration to the individual. This method avoids the decomposition of vitamin D which occurs in solutions of vitamin D. Solutions which may comprise tachysterol, lumisterol and derivatives thereof may include the above-listed parental solutions. Of course, the solutions comprising tachysterol, lumisterol and derivatives thereof must be stored in an opaque container to avoid premature conversion of tachysterol, lumisterol and derivatives to the corresponding vitamin D compound.

Having now generally described this invention, the same will be understood by reference to an example which is provided herein for purposes of illustration only and is not intending to be limited unless otherwise specified.

EXAMPLE 1

Figure 2A:
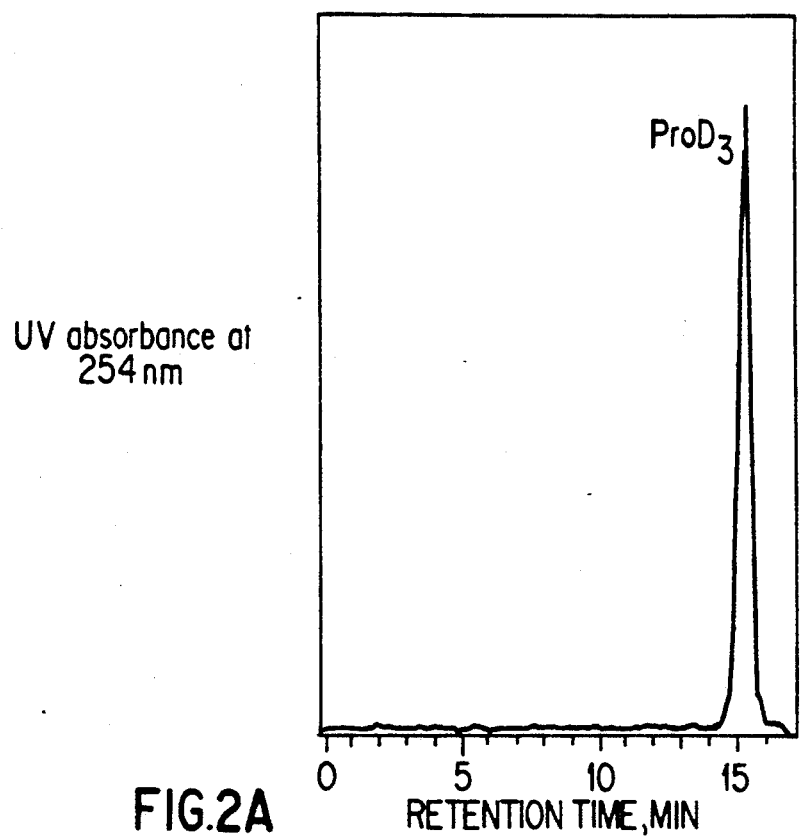
FIG. 2 depicts an HPLC trace of a control solution of provitamin $D_3$ (A) and a solution of winter (B).
Figure 2B:
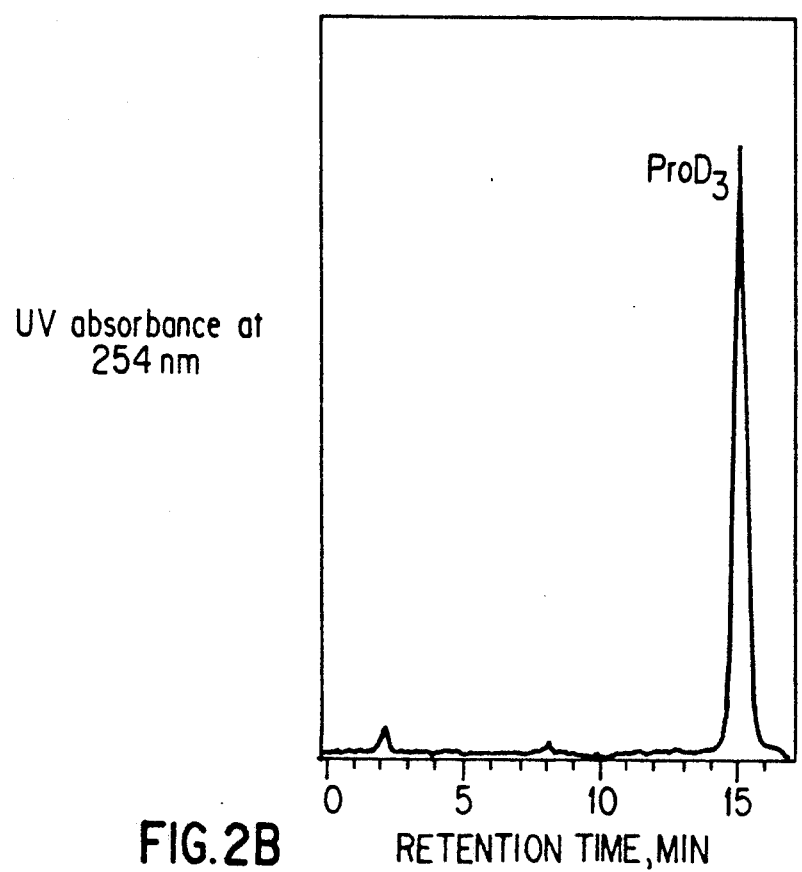
Figure 3A:
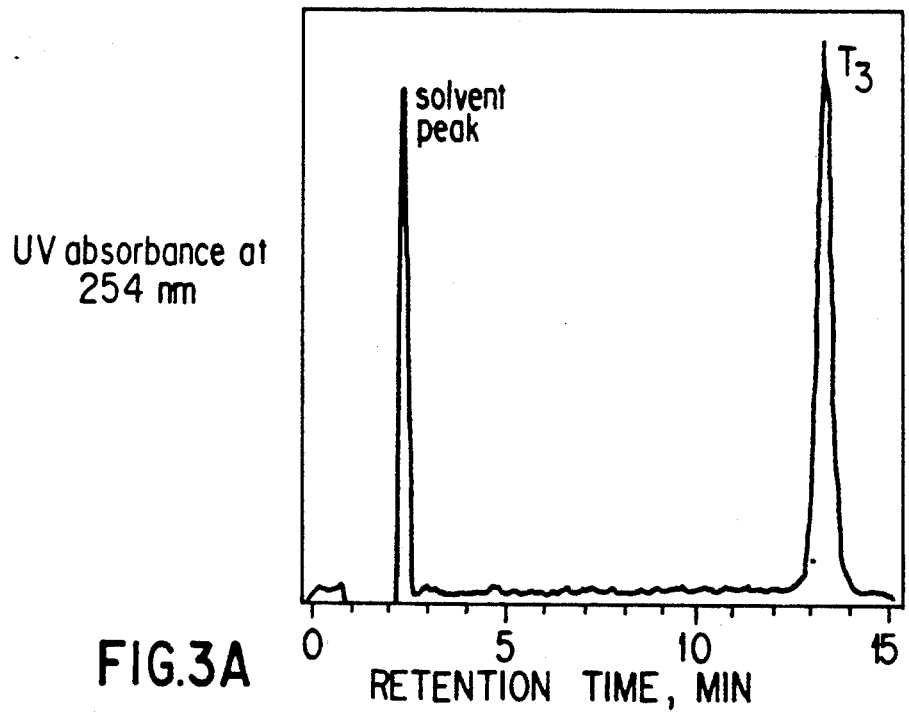
FIG. 3 depicts an HPLC trace of a control solution of tachysterol (A) and a solution of tachysterol exposed to sunlight on a day during the winter (B).
Figure 3B:
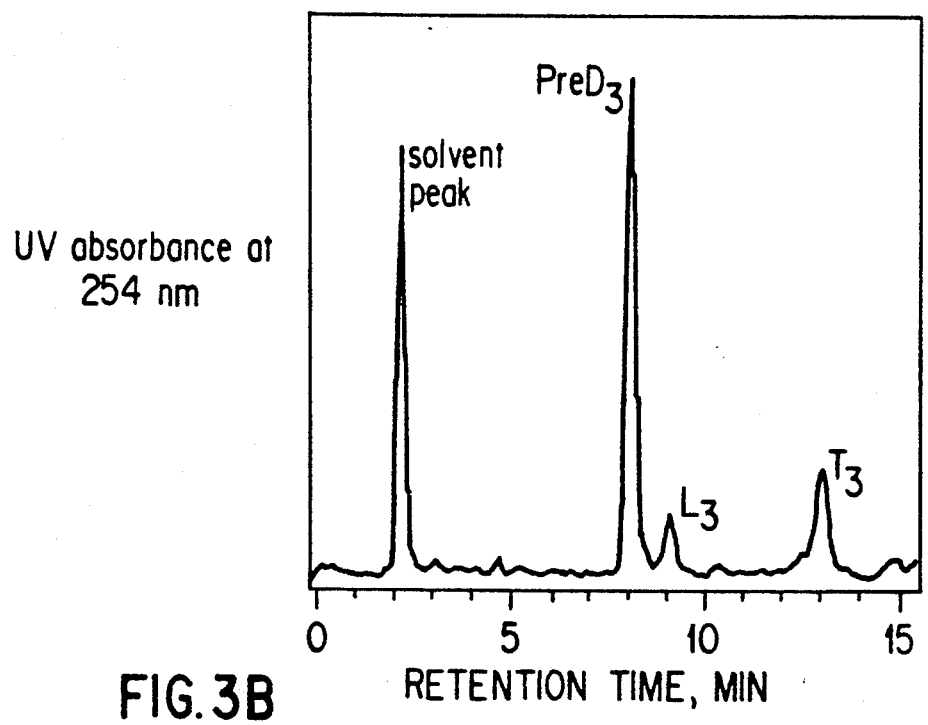
Figure 4A:
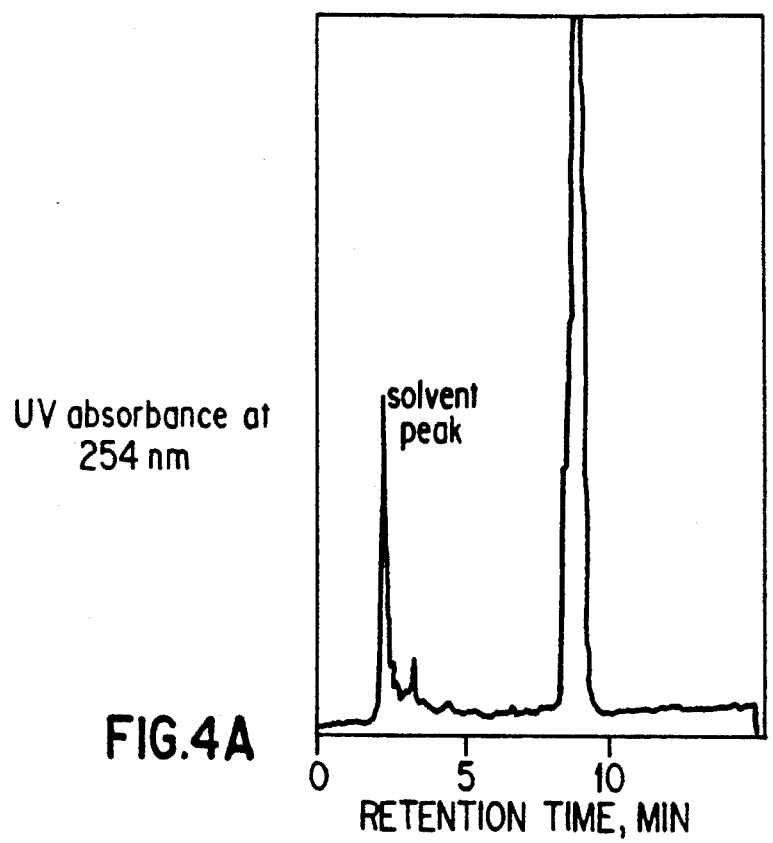
FIG. 4 depicts an HPLC trace of a control solution of lumisterol (A) and a solution of lumisterol exposed to sunlight on a day during the winter (B).
Figure 4B:
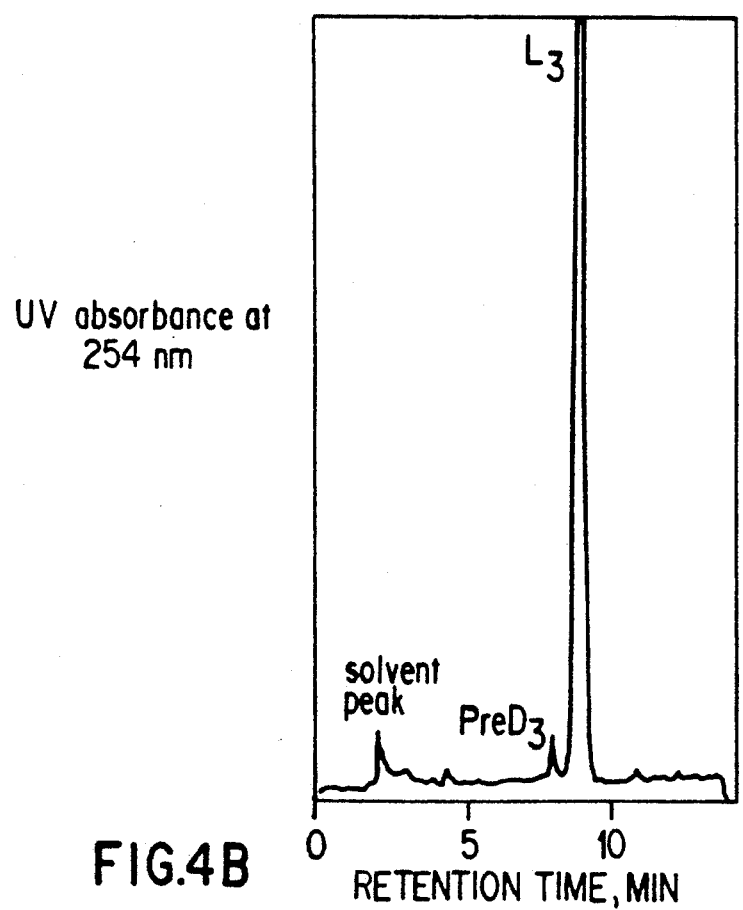

Crystalline provitamin $D_3$ was dissolved in methanol at a concentration of 10 micrograms/ml. Ten ml of this solution was placed in quartz test tubes. One test tube containing provitamin $D_3$ in methanol was exposed to direct sunlight in Boston during November, 1989 between 9 AM and 10 AM (FIG. 2B) while a similar sample remained in the dark over the same period of time (FIG. 2A). At the end of the exposure, a small aliquot was taken from each test tube and chromatographed on a high performance liquid chromatograph according to MacLaughlin et al., *Science* 216:1001-1003 (1982). Similar studies were conducted with lumisterol (FIG. 4) and tachysterol (FIG. 3) that were prepared as previously described (Holick et al., *Biochem.* 18:1003-1008 (1979). The analysis of all the chromatograms in FIGS. 2-4 revealed that when tachysterol and lumisterol were exposed to sunlight in November between 9 and 10 AM, they underwent photoisomerization to previtamin $D_3$ (FIGS. 3B, 4B). In contrast, provitamin $D_3$ exposed to the same direct sunlight did not convert to previtamin $D_3$ (FIG. 2B). All samples did not convert to previtamin $D_3$ (FIGS. 2A, 3A, 4A).

Having now generally described this invention, it will be apparent to one of ordinary skill in the art that the same can be carried out in a variety of embodiments and variations which are equivalent without affecting the spirit or scope of the invention or any embodiments thereof.

What is claimed is:

1. A composition formulated for topical or intravenous administration comprising a pharmaceutically acceptable carrier and a compound having the formula:

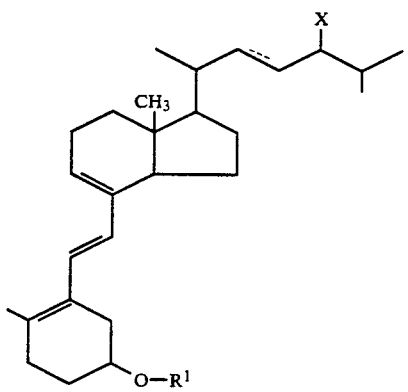

wherein the bond between C-22 and C-23 is a single or double bond;

X is hydrogen, methyl or ethyl; and $R^1$ is hydrogen or a straight or branched chain glycosidic residue containing 1-20 glycosidic units per residue, or $R^1$ is an orthoester glycoside moiety of the formula:

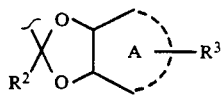

where A represents a glucofuranosyl or a glucopyranosyl ring;

$R^2$ is hydrogen lower ($C_1$-$C_4$) alkyl, $C_7$-$C_{10}$ aralkyl, or $C_6$-$C_{10}$ aryl; and $R_3$ is hydrogen or a straight or branch chain glycosidic residue containing 1-20 glycosidic units per residue; and wherein said compound is present in an amount effective to provide vitamin D to an individual when exposed to UV radiation of greater than 315 nm which is insufficient to effect the photoisomerization of provitamin D to previtamin D.

2. The composition of claim 1, wherein said compound is tachysterol$_3$.

3. The composition of claim 1, wherein said carrier is effective for topical administration.

4. The composition of claim 3, further comprising one or more sun screen agents.

5. The composition of claim 1, wherein said carrier is effective for intravenous administration.

6. The composition of claim 1, wherein said compound is present in an amount of 0.00001 to 10% by weight.

7. The composition of claim 1, wherein said compound is present in an amount of 0.0001 to 0.01% by weight.

8. A method for providing vitamin $D_3$ to an individual which comprises administering to said individual an effective amount of the pharmaceutical composition of claim 1 and exposing said individual to UV radiation.

9. The method of claim 8, wherein said composition is administered by topical means.

10. The method of claim 9, wherein said composition further comprises one or more sun screen agents.

11. The method of claim 8, wherein said composition is administered by intravenous means.

12. The method of claim 8, wherein said UV radiation has a wavelength of greater than about 315 nm which is insufficient to effect the photoisomerization of provitamin D to previtamin D.

13. A method for treating or preventing osteomalacia due to vitamin D deficiency or a calcium disorder resulting from a lack of vitamin D, glucocorticoid-induced decrease in calcium absorption, osteoporosis, senile decrease in calcium adsorption, hypoparathyroidism, milk fever disease, or turkey weak leg disease in an individual which comprises administering to said individual an effective amount of the pharmaceutical composition of claim 1 and exposing said individual to UV radiation.

14. The method of claim 13, wherein said composition is administered by topical means.

15. The method of claim 14, wherein said composition further comprises one or more sun screen agents.

16. The method of claim 13, wherein said composition is administered by intravenous means.

17. The method of claim 13, wherein said UV radiation has a wavelength of greater than about 315 nm which is insufficient to effect the conversion of provitamin D to previtamin D.

* * * * *